(12) United States Patent
Miller (10) Patent No.: US 8,685,108 B2
(45) Date of Patent: Apr. 1, 2014

(54) MODULAR PROSTHETIC FOOT

(75) Inventor: Joseph A. Miller, Fredericksburg, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/437,994

(22) Filed: Apr. 3, 2012

(65) Prior Publication Data

US 2012/0191222 A1 Jul. 26, 2012

Related U.S. Application Data

(63) Continuation of application No. 12/096,283, filed as application No. PCT/US2006/062472 on Dec. 21, 2006, now Pat. No. 8,172,909.

(60) Provisional application No. 60/756,623, filed on Dec. 22, 2005.

(51) Int. Cl.
*A61F 2/68* (2006.01)

(52) U.S. Cl.
USPC ............................................................ 623/53

(58) Field of Classification Search
USPC ................................................. 623/47, 53
See application file for complete search history.

(56) References Cited

U.S. PATENT DOCUMENTS

| | | | |
|---|---|---|---|
| 2,731,645 A | 1/1956 | Woodall | |
| 4,007,497 A | 2/1977 | Werner | |
| 5,030,239 A | 7/1991 | Copes | |
| 5,181,933 A | 1/1993 | Phillips | |
| 5,571,213 A | 11/1996 | Allen | |
| 5,766,264 A * | 6/1998 | Lundt | 623/47 |
| 6,290,730 B1 * | 9/2001 | Pitkin et al. | 623/49 |
| 6,379,393 B1 | 4/2002 | Mavroidis et al. | |
| 7,108,723 B2 | 9/2006 | Townsend et al. | |
| 2002/0082712 A1 * | 6/2002 | Townsend et al. | 623/52 |
| 2002/0143408 A1 | 10/2002 | Townsend et al. | |
| 2008/0228288 A1 | 9/2008 | Nelson et al. | |
| 2008/0300692 A1 | 12/2008 | Moser et al. | |

FOREIGN PATENT DOCUMENTS

| | | |
|---|---|---|
| JP | 5146796 | 4/1976 |
| JP | 05-076557 | 3/1993 |
| JP | 09-084814 | 3/1997 |
| WO | 8806431 A1 | 9/1988 |

OTHER PUBLICATIONS

English Abstract of JP 09-084814.
English Abstract of JP 05-076557.
Huson, A., "Joints and Movements of the Foot: Terminology and Concepts," Acta Morphol. Neerl.-Scand., 25 (1987), pp. 117-130.

* cited by examiner

*Primary Examiner* — David Isabella
*Assistant Examiner* — Jacqueline Woznicki
(74) *Attorney, Agent, or Firm* — Elizabeth Arwine (57) ABSTRACT

A modular prosthetic foot includes an ankle component; a forefoot component having a circular part with a rounded top surface and at least one flat side surface, the circular part being connected to a rear part of the forefoot component; a forefoot cushion bumper positioned around the circular part; and a heel component.

19 Claims, 7 Drawing Sheets

MODULAR PROSTHETIC FOOT

This application is a Continuation Application of U.S. Ser. No. 12/096,283, filed on Jun. 5, 2008, in the U.S. Patent and Trademark Office, which is a U.S. national stage application of PCT international stage application PCT/US2006/062472 filed on Dec. 21, 2006 and, which claims priority of U.S. provisional application Ser. No. 60/756,623 filed on Dec. 22, 2005.

FIELD OF THE INVENTION

This invention relates to a modular prosthetic foot. The modular prosthetic foot may be utilized worldwide in a variety of climates or terrains. The simple and durable design of the modular prosthetic foot makes it useful for almost any lower extremity amputee.

BACKGROUND OF THE INVENTION

Prosthetic ankles and feet are known. For example, U.S. Pat. No. 5,030,239 discloses a biomechanical ankle which imitates the three primary categories of movement in a human foot. Parallel sole and limb supporting plates are held in spaced relationship by an upright post. The limb supporting plate is connected to the post with a ball and socket joint. A helical spring is fixed between the plates to provide resilient support to the anterior portion of the foot in imitation of normal muscular control. The ball and socket joint, in cooperation with the spring, permits the biomechanical ankle to imitate the inversion-eversion, plantar flexion-dorsiflexion, and lateral rotation found in a normal human foot.

U.S. Pat. No. 7,108,723 B2 discloses a prosthesis for improving the gait and comfort qualities of the amputee that participates in walking, running and jumping activities. A foot and an ankle of the prosthesis are monolithically formed as a resilient member including a strut which forms an ankle joint. A hole extends through the resilient member with the periphery of the hole forming an anterior side surface of the strut. The resilient member anterior to the hole includes a gap to permit motion about the ankle joint axis while providing a stop in dorsiflexion. The hole is elongated upwardly such that the strut is upstanding and anterior convexly curved.

However, there remains a need for a modular prosthetic foot, in particular, a modular prosthetic foot that mimics the subtalar joint of a human foot.

SUMMARY OF THE INVENTION

In an aspect of the invention, a modular prosthetic foot is provided characterized by an ankle component; a forefoot component having a circular part with a rounded top surface and at least one flat side surface, said circular part being connected to a rear part of the forefoot component; a forefoot cushion bumper positioned around the circular part; and a heel component.

In another aspect of the invention, a front part of the ankle component is about 5° to about 20° higher than a rear part of the ankle component.

In another aspect of the invention, the ankle component further comprises an orifice for connection to part of a prosthesis or to a pylon.

In another aspect of the invention, the prosthetic foot is provided with a microprocessor device.

Given the following enabling description of the drawings, the apparatus should become evident to a person of ordinary skill in the art.

DETAILED DESCRIPTION OF THE DRAWINGS

Figure 1:
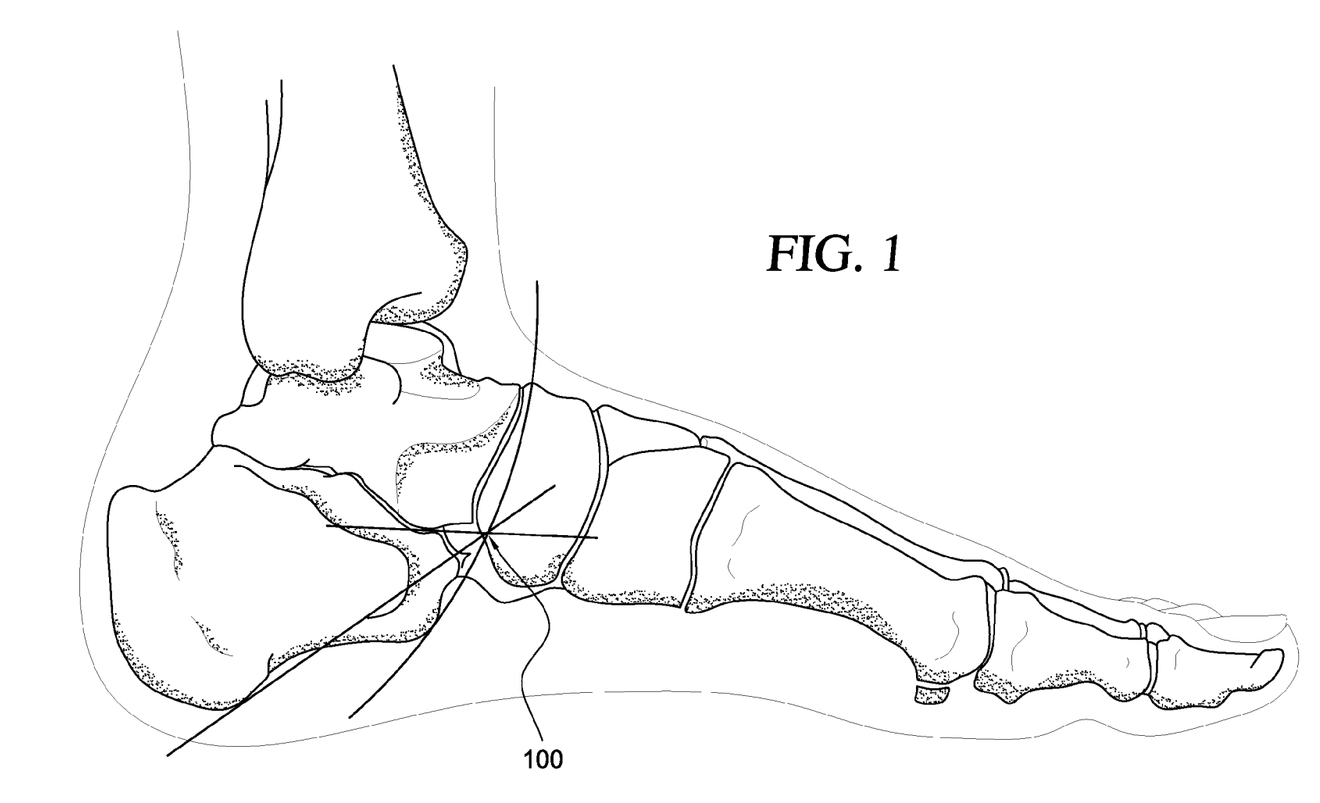
FIG. 1 is a schematic side view of a human foot showing the subtalar joint.

FIGS. 1-11 illustrate a modular prosthetic foot according to the invention. The invention is an anatomically-based modular prosthetic foot. The prosthetic foot was designed based on the kinesiology of the anatomical foot. In particular, the structure of the prosthetic foot is focused on mimicking the subtalar joint 100, as shown in FIG. 1. Anatomically, if the tibia internally rotates the subtalar joint everts (pronates). Conversely, if the tibia is externally rotated, the subtalar joint inverts (supinates). Thus, in theory, the subtalar joint functions as an elliptical hinge.

In this detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

Figure 2:
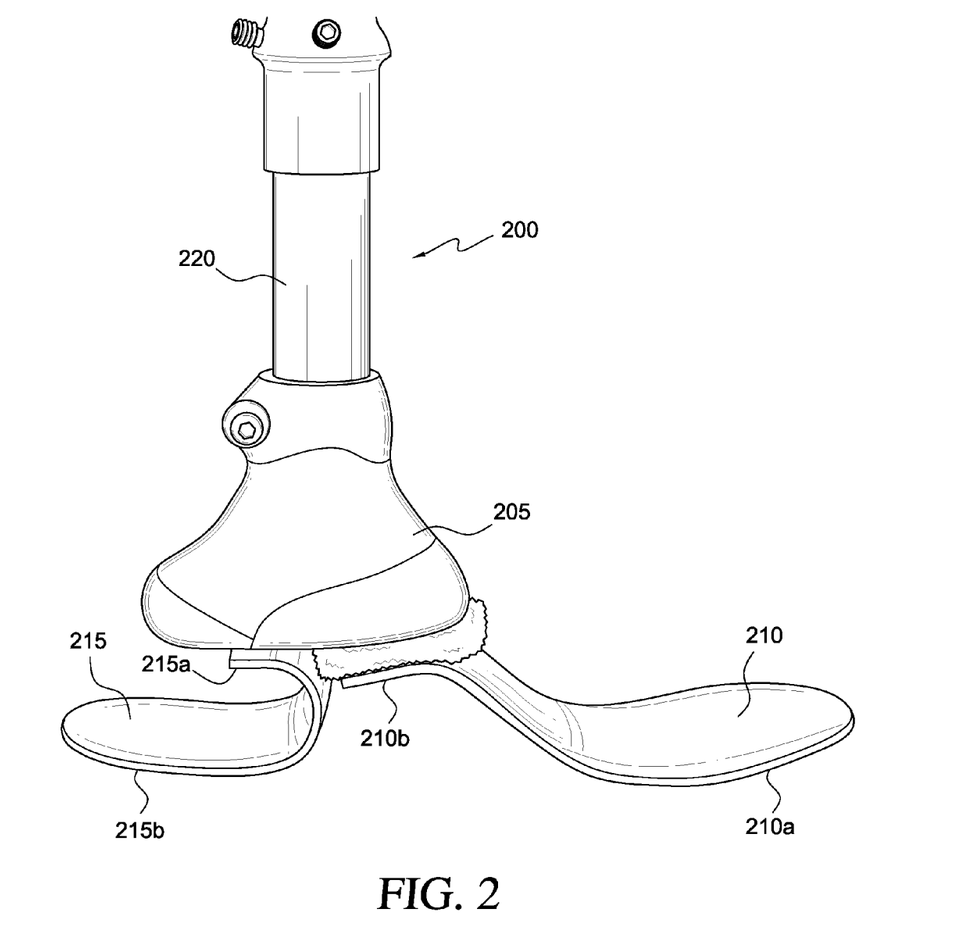
FIG. 2 is a side view of a modular prosthetic foot according to an embodiment of the invention connected to pylon.

The prosthetic foot of the invention is modular, thereby accommodating variability in individual subjects and the required functions. As shown in FIG. 2, prosthetic foot 200 comprises three basic components: (1) a middle section, referred to as an ankle component 205; (2) a toe section, referred to as the forefoot component 210; and (3) a heel section, referred to as the heel component 215. The forefoot component 210 has a front part 210a and a rear part 210b. The heel component 215 has a front part 215a and a rear part 215b.

A. Ankle Component

The ankle component is a unitary body of any effective shape and size allowing connection to both the heel component and the forefoot component.

Figures 3, 4:
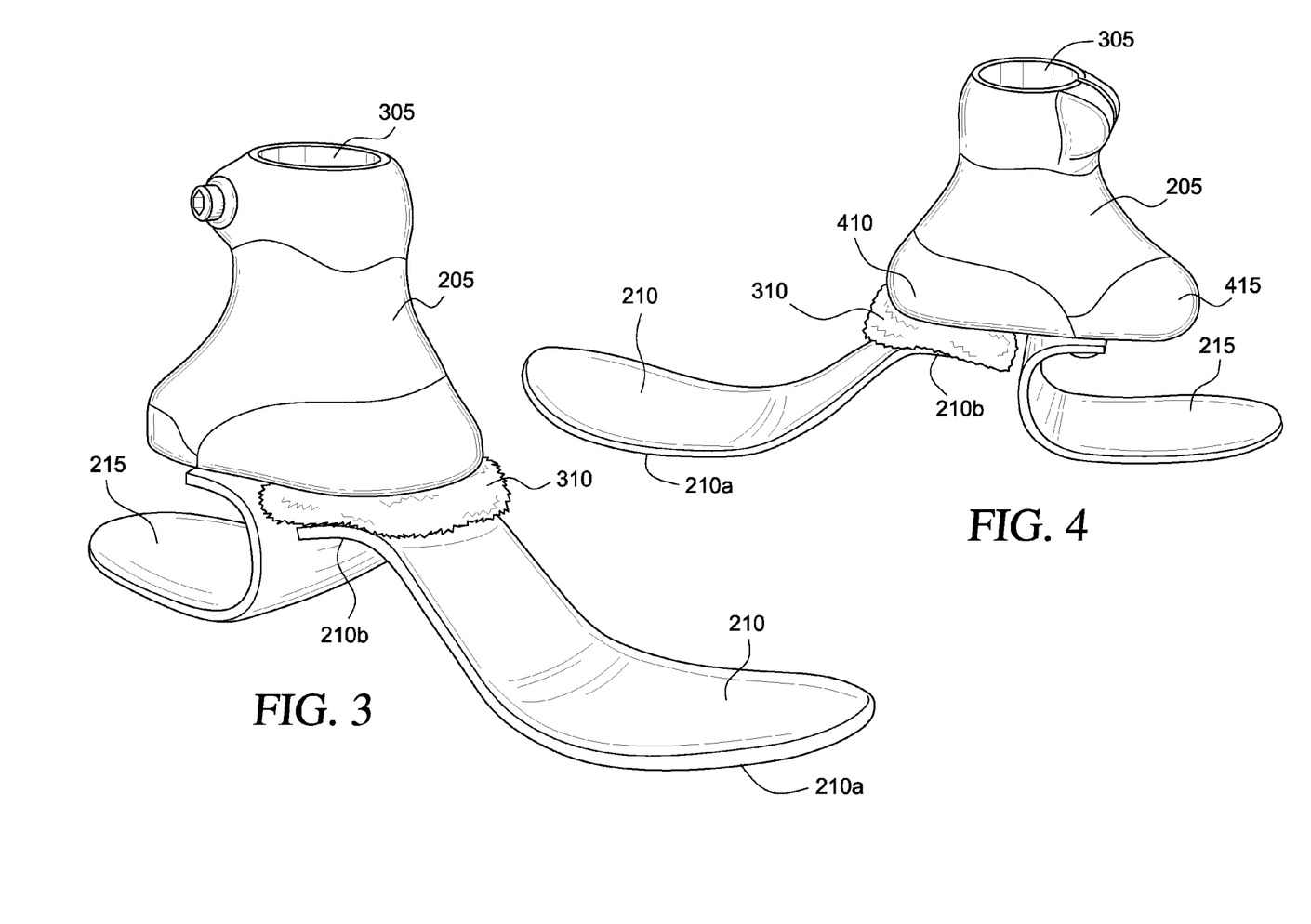
FIG. 3 is a perspective view of the modular prosthetic foot according to an embodiment of the invention.
FIG. 4 is a side view of the modular prosthetic foot according to an embodiment of the invention.
Figure 8:
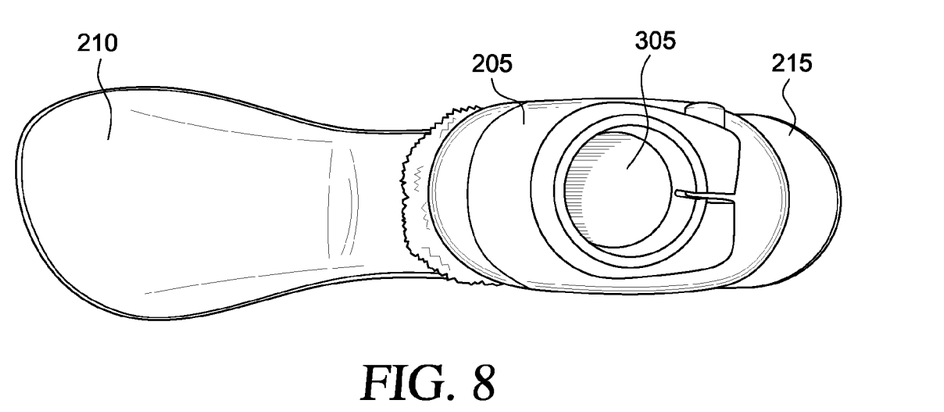
FIG. 8 is a top view of the modular prosthetic foot according to an embodiment of the invention.

The ankle component 205 may be connected to part of a prosthesis or to a pylon 220, as shown in FIG. 2. Accordingly, the ankle component comprises a receptacle or orifice 305 for connection to the part of a prosthesis or pylon, as shown in FIGS. 3-4 and 8. Connection to part of a prosthesis or connection to a pylon are the two most common methods of attachment for endoskeletal or exoskeletal prosthetic systems used through the world. In embodiments, the receptacle or orifice 305 may be present on a surface of the ankle component 205 which is opposite a surface to which the forefoot component 210 and the heel component 215 are connected or mounted. The ankle component may be connected to the prosthesis part or to the pylon by at least one connector. The connector may be, but is not limited to, a pin, screw, bolt, shaft, an adhering compound, or any combination thereof.

B. Forefoot Component

The forefoot component may be of any effective shape and size. In embodiments, the forefoot component may have an elliptical shape, a J-shape, a C-shape, or an S-shape.

Figure 9:
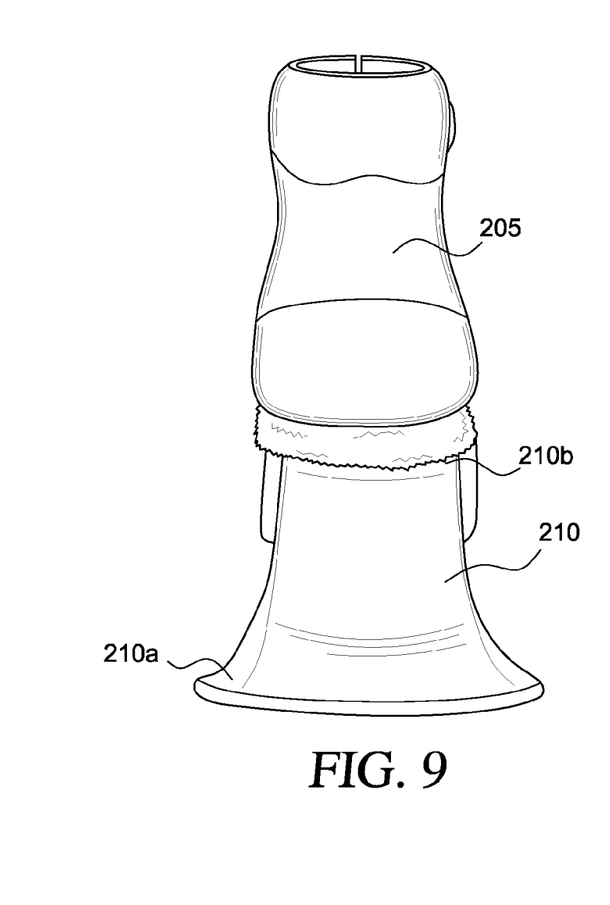
FIG. 9 is a front view of the modular prosthetic foot according to an embodiment of the invention.

As shown in FIGS. 2 and 9, the rear part 210b of the forefoot component 210 is connected to the ankle component 205.

Figures 5, 6A, 6B, 6C, 6D:
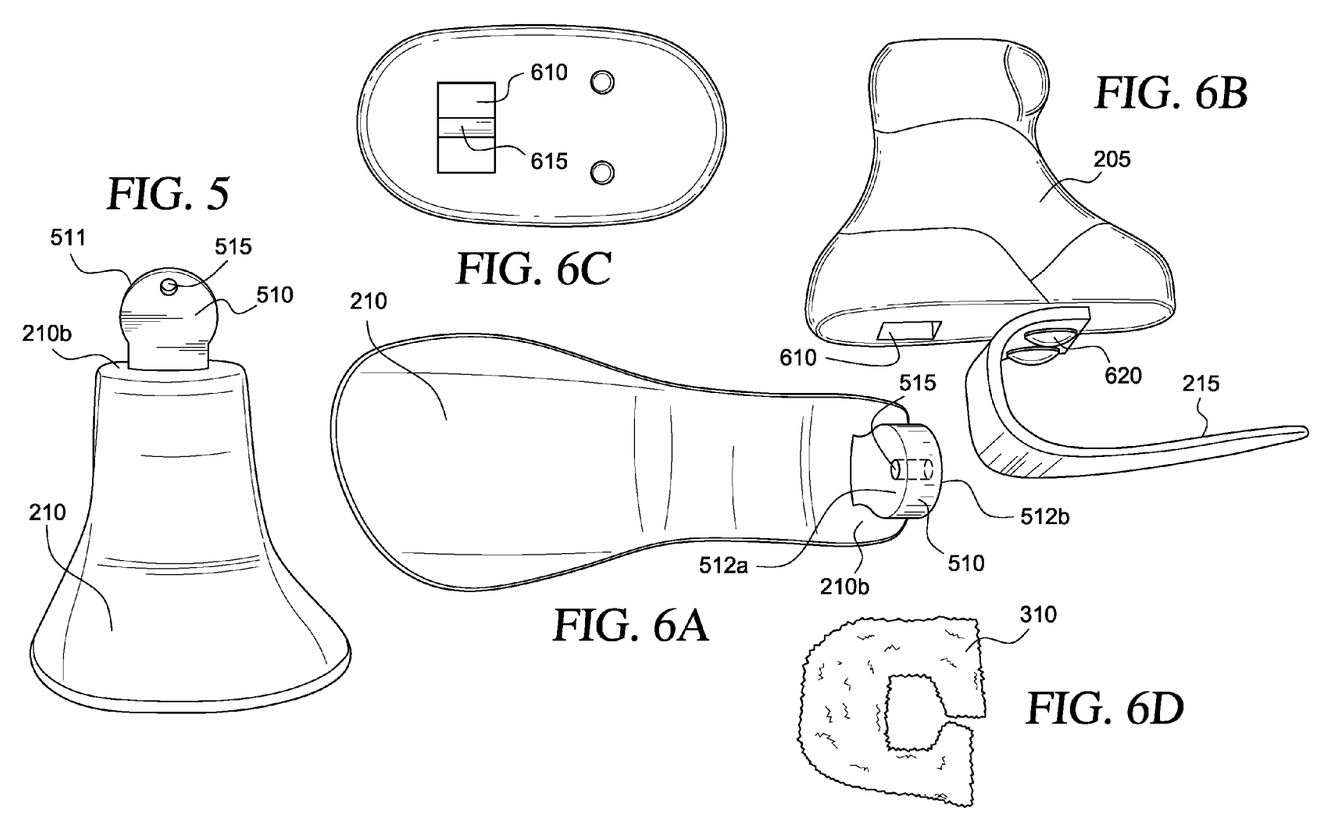
FIG. 5 is a front view of the forefoot component of the modular prosthetic foot according to an embodiment of the invention.
FIG. 6A is a top view of the forefoot component of the modular prosthetic foot according to an embodiment of the invention.
FIG. 6B is a side view of the ankle component and heel component of the modular prosthetic foot according to an embodiment of the invention.
FIG. 6C is a bottom view of the ankle component of the modular prosthetic foot according to an embodiment of the invention.
FIG. 6D is a top view of the forefoot cushion bumper of the modular prosthetic foot according to an embodiment of the invention.

As shown in FIGS. 5 and 6A, the rear part of the forefoot component 210b comprises a circular part 510 having a rounded top surface 511 or convex top surface and at least one flat side surface. The circular part 510 preferably has two flat side surfaces 512a, 512b (i.e., a flat front surface and a flat back surface). In embodiments, the circular part 510 may have a hole 515 extending through its side surfaces, as shown in FIGS. 5 and 6A.

The circular part 510 fits into a slot or hole 610 located on a front part of the ankle component 205, as shown in FIGS. 6B-6C. A rod 615 in the ankle component 205 (as shown in FIG. 6C) may fit through the hole 515. Thus, the circular part 510 may rotate around the rod 615 in the ankle component. Alternatively, the circular part may have an indentation in its top surface, and the rod in the ankle component may fit or rest in the indentation.

As shown in FIG. 4, a front part 410 of the ankle component 205 is about 5° to about 25°, preferably about 10° to about 15°, higher than a rear part 415 of the ankle component to mimic the natural foot angle of the subtalar joint. Accordingly, the circular part 510 is set at an angle within the ankle component. The circular part is not perpendicular to an horizontal axis which is parallel to a level ground surface.

The structure of the circular part 510 and its angle within the ankle component allow it to pivot, simulating the subtalar joint of the natural foot (i.e., an elliptical hinge). Thus, the circular part everts (pronates) and inverts (supinates). In addition, the at least one flat surface of the circular part keeps the prosthetic foot from rotating too far forwards and/or too far backwards.

Figure 7:
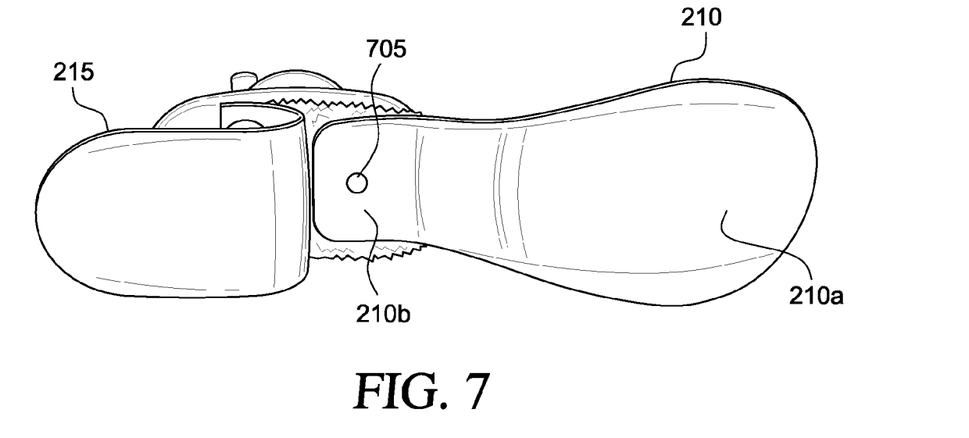
FIG. 7 is a bottom view of the modular prosthetic foot according to an embodiment of the invention.

In embodiments, the circular part may be connected or mounted to the forefoot component by at least one connector 705, as shown in FIG. 7. In embodiments, the connector may be, but is not limited to, a pin, screw, bolt, shaft, an adhering compound, or any combination thereof.

C. Forefoot Cushion Bumper

The motion (eversion and inversion) of the modular foot may be limited or controlled by a forefoot cushion bumper 310 positioned around the circular part, as shown in FIGS. 3-4. The forefoot cushion bumper 310 may be any effective shape and size. In embodiments, the forefoot cushion bumper may have a U-shape or a horseshoe-shape (FIG. 6D), thereby allowing it to clip around or be press fit around the circular part 510 on the rear part 210b of the forefoot component 210.

The forefoot cushion bumper controls the range of motion of the prosthetic foot and allows for compression. In embodiments, the forefoot cushion bumper may be made comprise a urethane, a dense foam, or an electro-responsive material, such as an electrically activated polymer or a piezoelectric material.

D. Heel Component

The heel component may be of any effective shape and size. In embodiments, the heel component may have an elliptical shape, a J-shape, a C-shape, or an S-shape.

Figure 10:
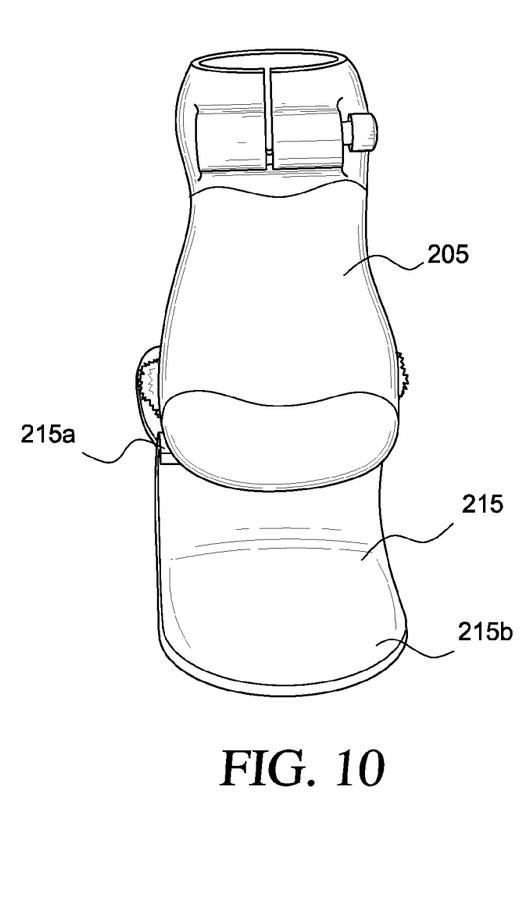
FIG. 10 is a rear view of the modular prosthetic foot according to an embodiment of the invention.

As shown in FIG. 2 and FIG. 10, a front part 215a of the rear component is connected to the ankle component 205. In embodiments, the heel component 215 may be mounted to the ankle component 205 by at least one connector 620, as shown in FIG. 6B. In embodiments, the connector may be, but is not limited to, a pin, screw, bolt, shaft, an adhering compound, or any combination thereof. The heel component may be connected to the bottom of the ankle component or to a side of the ankle component.

E. Microprocessor

In embodiments, the modular prosthetic foot of the invention may contain a microprocessor. The microprocessor may be located in any component of the prosthetic foot, but is preferably located in the forefoot component or forefoot cushion bumper. The at least one microprocessor device may allow for monitoring of how the person using the modular prosthetic foot walks.

Figure 11:
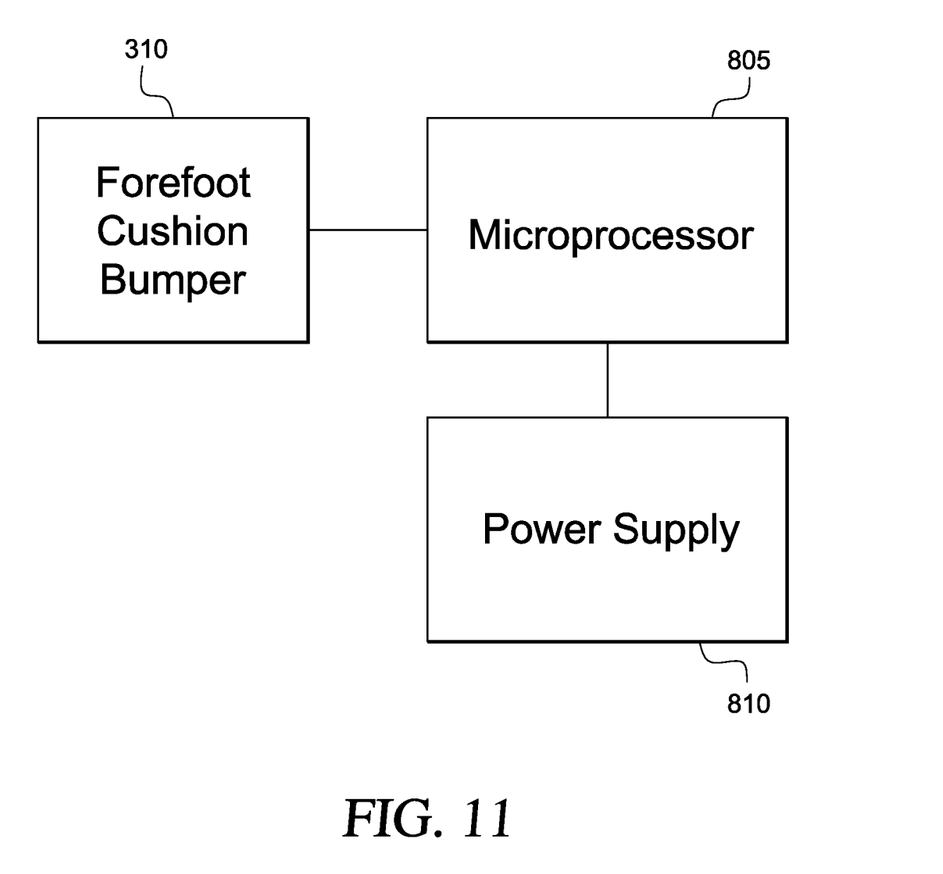
FIG. 11 is a block diagram of a microprocessor and forefoot cushion bumper according to an embodiment of the invention.

As shown in FIG. 11, a microprocessor 805 is connected to the forefoot cushion bumper 310 and to a power supply 810. Accordingly, the microprocessor 805 may monitor the forces in forefoot cushion bumper 310. In embodiments, the microprocessor may be programmed to change the density of an electro-responsive material of the forefoot cushion bumper, thereby allowing greater adaptation to the person's walking cycle for pliability and enhanced motion.

F. Modularity

The modularity of the prosthetic foot of the invention is advantageous. For example, one forefoot cushion bumper may be substituted with another forefoot cushion bumper having one or more different properties (e.g., different material, different thickness, different density, different shape) to vary the degree of motion or degree of compression. In addition, for a single ankle component, different forefoot components and different heel components may be interchanged.

This interchangeability allows for easy variation of the prosthetic foot to account for different shoe sizes or foot lengths. Obviously, one person may wear a men's shoe size 43 (U.S. shoe size 10), and another person may wear a men's shoe size 39 (U.S. shoe size 7). If the ankle component is the same for both people, proper heel components and forefoot components may be readily chosen.

The interchangeability also allows for variation of the prosthetic foot based upon at least one of the individual's height, weight, degree of physical activity, or any combination thereof. For example, the heel component and/or forefoot component may be designed to offer more or less compression based on at least one of an individual's activity, weight, height, or a specific gait pattern. In addition, at least one of the material, shape, size, density, or method of attachment to the ankle component may have an effect on movement and may accordingly be chosen based upon the specific needs of an individual. The interchangeability also allows for easy replacement of a component that may be found to be defective or broken.

A health practitioner evaluating an individual, for example a patient, may order at least one of the appropriate heel component or forefoot component from a component list which has a scaled matrix to assist in ordering the correct component. Bench testing may be used to establish the scaled matrix. Therefore, the invention can be made adaptable and suitable depending on many variables.

Any suitable material may be used for the various component parts of this prosthetic foot of the invention. In embodiments, the entire prosthetic foot or any one of the ankle component, the forefoot component, or the heel component may be manufactured from a carbon fiber material. Carbon fiber material achieves the characteristic functions of energy return and modularity. As noted, the forefoot cushion bumper may comprise a urethane, a dense foam, or an electro-responsive material, such as an electrically activated polymer or a piezoelectric material.

The shape of the various component parts is not limited to that described or illustrated herein. Any shape of a component part may be used so long as the purpose for which the invention is intended. One having ordinary skill in the art would be able to identity suitable materials and/or shapes of component parts to employ within the scope of the present invention.

Although the present invention has been described in terms of particular exemplary and alternative embodiments, it is not limited to those embodiments. Alternative embodiments, examples, and modifications which would still be encompassed by the invention may be made by those skilled in the art, particularly in light of the foregoing teachings.

What is claimed is:

1. A modular prosthetic foot, comprising:
    an ankle component having a slot in a front part of the ankle component;
    a forefoot component comprising a circular part with a rounded top surface and at least one flat side surface, said circular part being connected to a rear part of the forefoot component and being fit into the slot;
    a forefoot cushion bumper positioned around the circular part; and
    a heel component connected to a rear bottom of the ankle component,
    wherein the front part of the ankle component is about 5° to about 25° higher than a rear part of the ankle component with respect to a horizontal axis parallel to a level ground surface when the circular part is set at an angle within the ankle component,
    wherein the at least one flat side surface of the circular part comprises a flat front surface that faces towards a front of the forefoot component and a flat back surface that faces towards a back of the forefoot component.

2. The modular prosthetic foot of claim 1, wherein the front part of the ankle component is about 10° to about 15° higher than the rear part of the ankle component with respect to the horizontal axis parallel to the level ground surface.

3. The modular prosthetic foot of claim 1, wherein the circular part has a hole extending from the flat front surface to the flat back surface through which a rod in the slot of the ankle component fits.

4. The modular prosthetic foot of claim 1, wherein the circular part has an indentation in its top surface in which a rod in the ankle component fits.

5. The modular prosthetic foot of claim 1, wherein the ankle component further comprises an orifice for connection to part of a prosthesis or to a pylon.

6. The modular prosthetic foot of claim 1, further comprising a microprocessor device located in any component of the modular prosthetic foot.

7. The modular prosthetic foot of claim 1, wherein the forefoot cushion bumper comprises a microprocessor device for monitoring how a person using the modular prosthetic foot walks.

8. The modular prosthetic foot of claim 1, wherein said forefoot cushion bumper comprises an electrically activated polymer or a piezoelectric material.

9. The modular prosthetic foot of claim 1, wherein said forefoot cushion bumper comprises a urethane material.

10. The modular prosthetic foot of claim 1, wherein said ankle component, said forefoot component, and said heel component comprise a carbon fiber material.

11. The modular prosthetic foot of claim 1, wherein different forefoot components and different heel components may be interchanged based upon at least one of an individual's height, weight, degree of physical activity, or any combination thereof.

12. The modular prosthetic foot of claim 1, wherein the circular part simulates an anatomically-based elliptical hinge that everts and inverts.

13. The modular prosthetic foot of claim 1, wherein the circular part is directly connected to the ankle component by at least one connector comprising a pin, screw, bolt, shaft, adhering compound, or any combination thereof.

14. The modular prosthetic foot of claim 1, wherein the ankle component, forefoot component, and heel component are three separate components.

15. The modular prosthetic foot of claim 14, wherein said forefoot component is connected to the front part of the ankle component and said heel component is connected to the rear part of the ankle component.

16. The modular prosthetic foot of claim 1, wherein the circular part and its angle within the ankle component allow the circular part to pivot, thereby simulating a subtalar joint of a natural foot.

17. The modular prosthetic foot of claim 1, wherein the circular part comprises a rounded top surface and two flat side surfaces, and pronates and supinates.

18. The modular prosthetic foot of claim 1, wherein the circular part extends upwardly from the rear part of the forefoot component.

19. The modular prosthetic foot of claim 1, wherein the ankle component has a planar bottom surface.

* * * * *